US006605813B1

(12) United States Patent
Kovalsky et al.

(10) Patent No.: US 6,605,813 B1
(45) Date of Patent: Aug. 12, 2003

(54) BENCHTOP FLUORESCENCE MOLECULAR BEACONS DETECTOR AND READER

(75) Inventors: Alvin Kovalsky, Paramount, CA (US); Max D. Miller, Manhattan Beach, CA (US)

(73) Assignee: BHK, Inc., Claremont, CA (US)

( * ) Notice: Subject to any disclaimer, the term of this patent is extended or adjusted under 35 U.S.C. 154(b) by 73 days.

(21) Appl. No.: 09/676,608

(22) Filed: Sep. 30, 2000

Related U.S. Application Data
(60) Provisional application No. 60/158,609, filed on Oct. 9, 1999.

(51) Int. Cl.[7] .............................................. G01N 21/64
(52) U.S. Cl. .................................. 250/458.1; 250/461.2
(58) Field of Search .......................... 250/458.1, 459.1, 250/461.1, 461.2; 356/417, 317, 318; 422/82.08, 82.11

(56) References Cited

U.S. PATENT DOCUMENTS

| | | | | |
|---|---|---|---|---|
| 4,671,662 A | * | 6/1987 | Zupanick et al. | 250/458.1 |
| 4,922,092 A | * | 5/1990 | Rushbrooke et al. | 250/214 VT |
| 5,169,601 A | * | 12/1992 | Ohta et al. | 356/440 |
| 5,233,197 A | * | 8/1993 | Bowman et al. | 250/461.1 |
| 5,958,907 A | * | 9/1999 | Welsh | 424/601 |
| 6,084,669 A | * | 7/2000 | Schmid | 356/318 |
| 6,144,448 A | * | 11/2000 | Mitoma | 250/458.1 |
| 6,198,107 B1 | * | 3/2001 | Seville | 250/458.1 |
| 6,211,953 B1 | * | 4/2001 | Niino et al. | 250/458.1 |
| 6,352,672 B1 | * | 3/2002 | Mabile et al. | 250/458.1 |

FOREIGN PATENT DOCUMENTS

| | | | | |
|---|---|---|---|---|
| WO | WO 98/01743 | * | 1/1998 | G01N/21/64 |

* cited by examiner

*Primary Examiner*—Constantine Hannaher
*Assistant Examiner*—Albert Gagliardi
(74) *Attorney, Agent, or Firm*—Boniard I. Brown (57) ABSTRACT

A low cost benchtop molecular beacons (oligonucleotide probes) reader utilizes an array of light emitting diodes to excite the fluorescence of the reaction of the combining of the molecular beacons with actual DNA strands. If the Molecular beacons match with the DNA the reaction will fluoresce a known wavelengths. If there is no match, the reaction will not fluoresce. The molecular beacons reader uses an array of light emitting diodes at given wavelengths. The unit also incorporates the proper filters depending on the wavelength required. The unit has interchangeable cartridges with the filters and light emitting diodes that can be easily changed. The system is used after the PCR process (polymerase chain reaction) and the samples are viewed in PCR strips or PCR plates directly out of a thermocycler. This unit serves as a low cost go-no-go test with easy to use equipment.

13 Claims, 10 Drawing Sheets

BENCHTOP FLUORESCENCE MOLECULAR BEACONS DETECTOR AND READER

RELATED APPLICATIONS

Reference is made to Applicants' Provisional Application No. 60/158,609, filed Oct. 9, 1999.

BACKGROUND OF INVENTION

1. Field of Invention

The present invention relates to the reading and the detection of the fluorescence of the reaction of the bonding of molecular beacons. The invention is intended as an inexpensive way to determine the results of the bonding of the molecular beacons with an actual DNA strand. These determinations can be used to determine the occurrence of viruses and other molecular presence.

2. Description of Prior Art

Molecular Beacons

Molecular beacons are oligtide probes that can report the presence of specific nucleic acids in homogeneous solutions. These probes were developed by the Public Health Research Institute of the City of New York, U.S. Pat. No. 5,925,517 by Tyagi, Kramer, and Lizardi. They are useful in situations where it is either not possible or desirable to isolate the probe-target hybrids from an excess of the hybridization probes, such as in real-time monitoring of polymerase chain reactions in sealed tubes or in detection of RNA within living cells. Molecular beacons are hairpin-shaped molecules with an internally quenched fluorophore whose fluorescence is restored when they bind to a target nucleic acid. They are designed in such a way that the loop portion of the molecule is a probe sequence complementary to a target nucleic acid molecule. The stem is formed by the annealing of complementary arm sequences on the ends of the probe sequence. A fluorescent moiety is attached to the end of one arm and a quenching moiety is attached to the end of the other arm. The stem keeps these two moieties in close proximity to each other, causing the fluorescence of the fluorophore to be quenched by energy transfer. Since the quencher moiety is a non-fluorescent chromophore and emits the energy that it receives from the fluorophore as heat, the probe is unable to fluoresce. When the probe encounters a target molecule, it forms a hybrid that is longer and more stable than the stem and its rigidity and length preclude the simultaneous existence of the stem hybrid. Thus, the molecular beacon undergoes a spontaneous conformational reorganization that forces the stem apart, and causes the fluorophore and the quencher to move away from each other, leading to the restoration of fluorescence which can be detected.

In order to detect multiple targets in the same solution, molecular beacons can be made in many different colors utilizing a broad range of fluorophores. DABCYL, a non-fluorescent chromophore, serves as the universal quencher for any fluorophore in molecular beacons. Owing to their stem, the recognition of targets by molecular beacons is so specific that single-nucleotide differences can be readily detected. Because of these properties molecular beacons have been used for detection of RNA within living cells for monitoring the synthesis of specific nucleic acids in sealed reaction vessels for homogenous one-tube assays for geno-typing single-nucleotide variations in DNA and for multi-plex PCR for the detection of four pathogenic retroviruses.

Detection Methods

Presently there are three methods for the reading of the molecular beacons. Using high pressure liquid chromatograph systems, Spectrofluorometers and thermal cyclers with a capacity to monitor fluorescence in real time. These approaches require expensive equipment and are large and complex. Present approaches limit the ability to do testing except at sophisticated laboratories.

3. References and Prior Art Statements

The inventors have also researched the literature and discuss the following patents:

1. U.S. Pat. No. 5,017,475 by Harte and Mastin describes a detection process based on a specific enzyme. The detection of a chemical reaction. The process uses fluorophore-labelled compound. The detection is based on using fluorescent dyes and inks.

2. U.S. Pat. No. 5,574,790 by Liang, Marinello, Ryan, Silverglate and Wray describes a Fluorescence authentication reader that is used with a computer program to determine the user determined and programable encryption of articles' authentic identity.

3. U.S. Pat. No. 5,666,417 by Liang, Marinello, Ryan and Wray describes a reader that performs the same functions as described in the U.S. Pat. No. 5,574,790 above in No. 2.

4. U.S. Pat. No. 5,686,300 by Berndt describes a fluorescence detection method and apparatus for detecting biological activities in a fluid specimen, such as blood, urine or sputum, where the specimen and a culture medium are introduced into a sealable container and exposed to conditions enabling a variety of metabolic, physical, and chemical changes to take place in the presence of microorganisms in the sample.

5. U.S. Pat. No. 5,719,061 by Rose-Pehrsson and Collins describes a method and apparatus for detection of hydrazine, monomethylhydrazine, and 1,1-dimethylhydrazine in air or other gas mediam or in an aqueous solution.

6. U.S. Pat. No. 5,723,294 by Glass, Coombs, Malmstrom and Wu describes a method and apparatus for permitting multiple PCR-amplified target nucleic acid sequence hybrids within a single sample, labeled with different fluorescent dyes, to be spectrally distinguished using data directly from a fluorescence reader instrument.

7. U.S. Pat. No. 5,861,256 by Glass, Coombs, Malmstrom and Wu describes a method and apparatus that performs the same function as U.S. Pat. No. 5,723,294 described above in No. 6.

SUMMARY OF THE PRESENT INVENTION

The molecular beacon reader allows the operator to view biological samples which have been treated with molecular beacon fluorophores to determine if the samples contain the material for which the molecular beacon is designed. The device illuminates the samples with a specific wavelength of light to excite the molecular beacons. There is a viewing port for the operator to observe the samples and also to photograph them. The device provides the proper light filters to discriminate between the excitation wavelength and the fluorescence. Provision is made for multiple samples to be read simultaneously.

DETAILED DESCRIPTION OF THE MOLECULAR BEACONS READER

The device consists of an adjustable light source with optical filters to control the wavelength. This light is fed into the sample chambers where the operator places the material to test. The sample chambers have viewing ports which contain optical filters to control the observed wavelength. There is an eyepiece attached to the enclosure for direct viewing by the user and/or a camera attachment for photography or video recording. There also may be auxiliary viewing ports for attachment of electronic sensors for computer analysis of the samples.

OPERATION

The basic operation of the Molecular Beacon Reader is as follows. The prepared samples are placed in the chambers and are illuminated by the excitation light beam. This light is produced by a light source which consists of a lamp or LED assembly with a power source, a filter assembly and a light delivery assembly. The excitation beam causes the fluorophores in the samples to glow at a characteristic wavelength. The glow from the samples is separated from the light from the excitation beam by an optical filter assembly and routed to the operator via an optics train. The operator may also attach a camera or video device for recording the results.

PREFERRED EMBODIMENT

Figure 1:
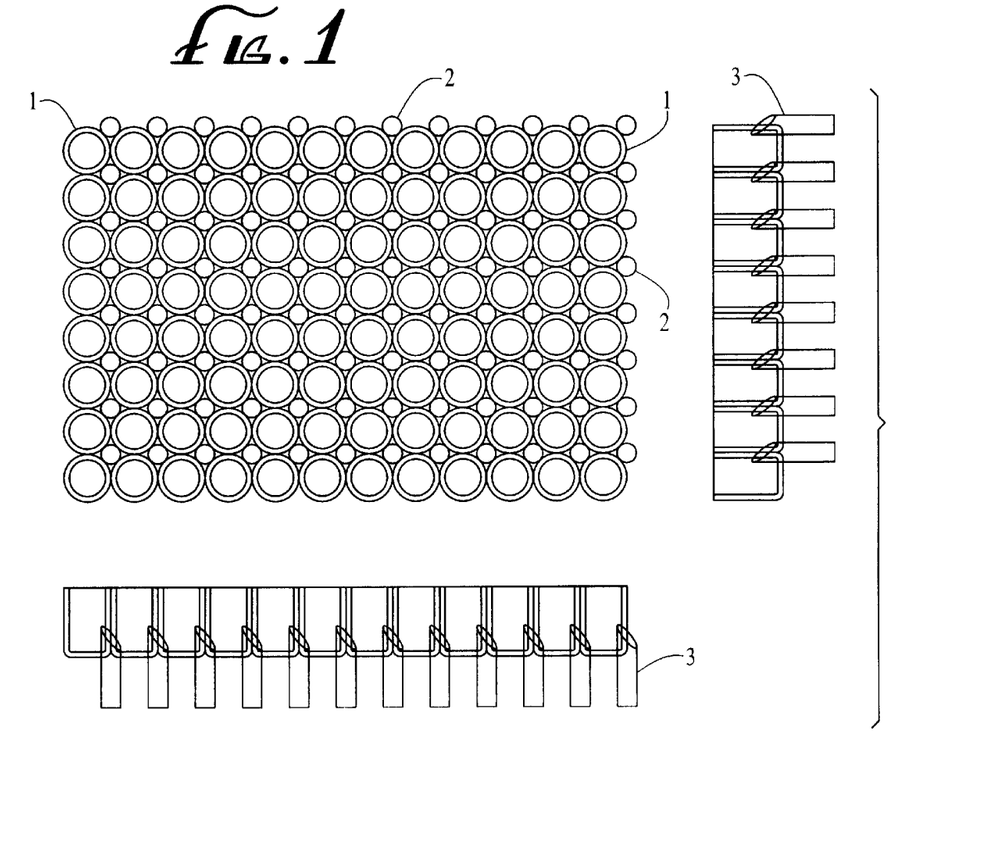
FIG. 1 shows an array of 96 sample chambers and the position of the fiber optics light guides. There can be from 12 to 384 chambers.
Figure 1A:
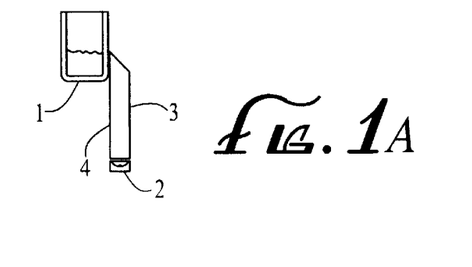
FIG. 1A is an enlarged view of a fiber light guide, diode and filter assembly of FIG. 1.
Figure 2:
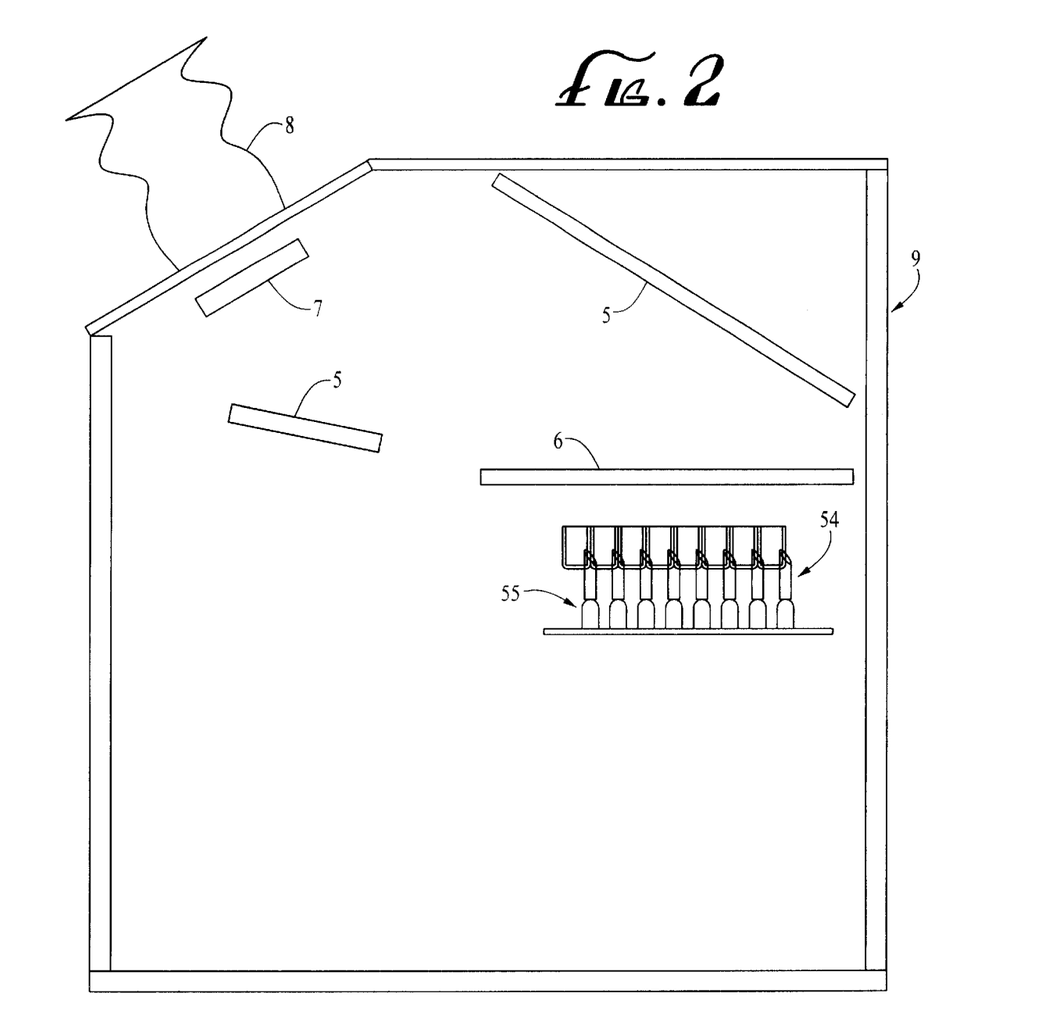
FIG. 2 shows the optical train and mirror setup for viewing the molecular beacons samples in relation to the sample chamber with the fiber optics light guide placement next to the samples.
Figure 3:
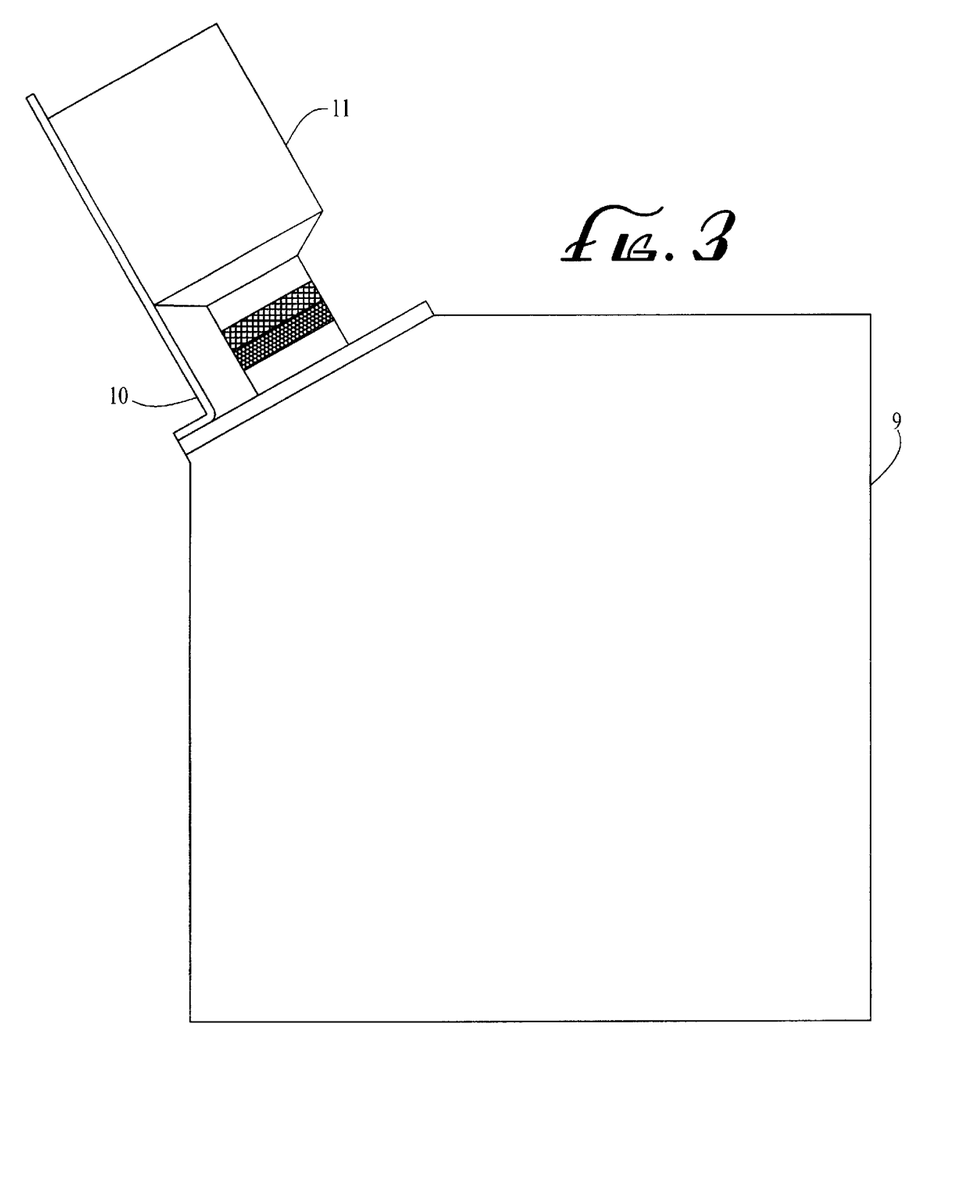
FIG. 3 shows the camera setup and placement for photographing the molecular beacons samples when required.

Referring to FIG. 1, the device consists of an array of sample chambers, 1, which may be a clear plastic tray arranged to hold a set of vials, or hold the sample directly. The excitation light source assembly, which consists of a set of light emitting diodes, 2, an optical fiber light guide, 3, and an optical filter assembly, 4, for each chamber sits below the chambers. The fiber optic light guides direct the excitation light into the chambers from the sides. The light emitting diode assembly, fiber optic light guide assembly and excitation filter assembly are replaceable by the operator for using different types of Molecular Beacons. Referring to FIG. 2, shows the position of the light emitting diode assembly, 54 and the fiber optic light guide, 55, the optical train consists of a mirror assembly, 5, an illuminated reticle, 6, an optical filter, 7, of the appropriate wavelength to block the excitation light referred to as the analyzer filter assembly, and an eyepiece assembly, 8, that allows the operator to view the samples from the top or optionally from the bottom. The analyzer filter assembly is user replaceable for use with different molecular beacons. The entire device is housed in a light tight box, 9, allowing use of the device in normal room lighting. The eyepiece assembly may be detached to allow the attachment of a camera bracket assembly, 10, to hold a camera, 11, in position for recording the experimental results as shown in FIG. 3.

Figure 4:
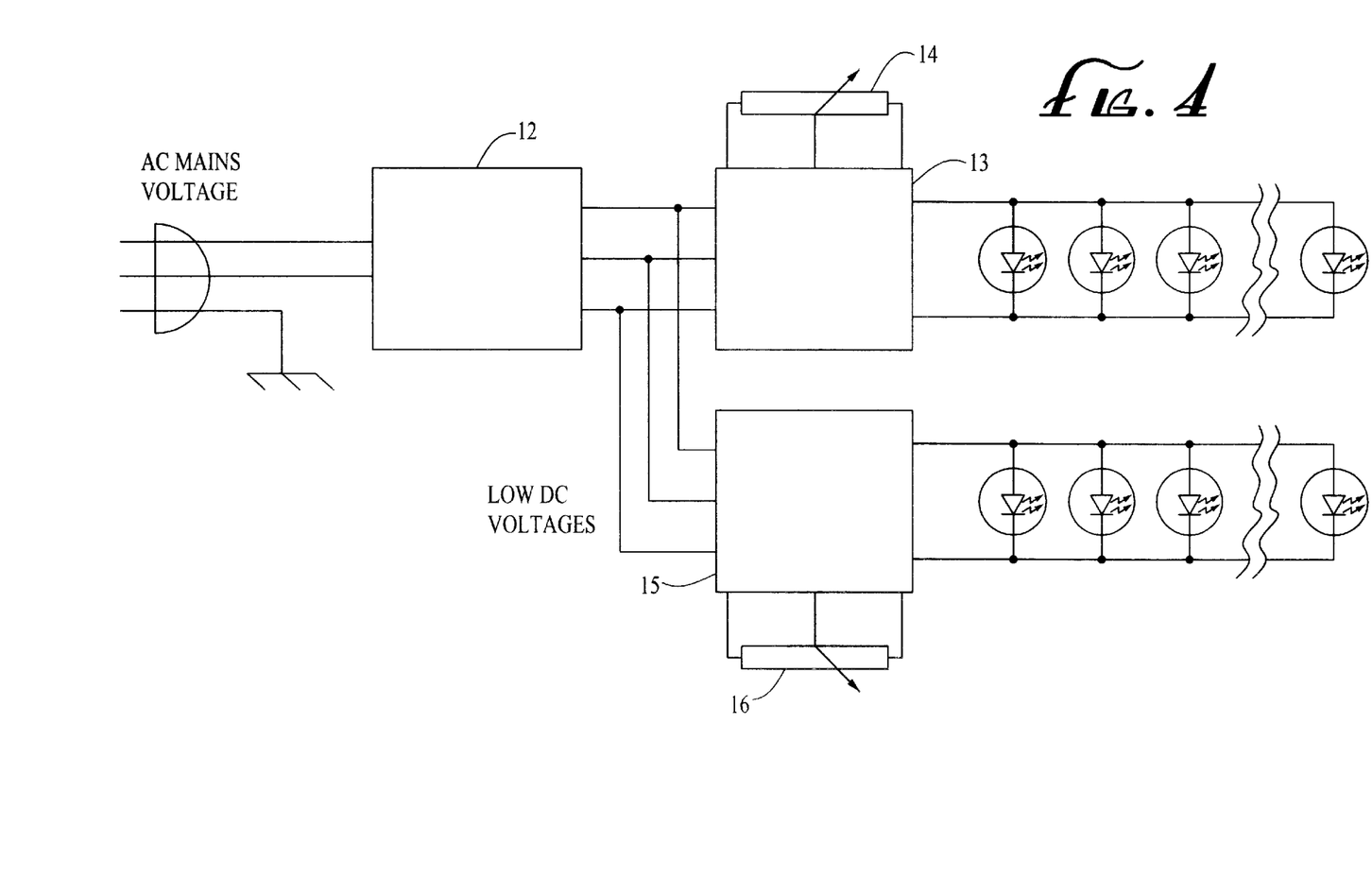
FIG. 4 is the power source for the led excitation.

FIG. 4 shows the power source for the light emitting diodes, which consists of a standard power supply, 12, which converts the AC line voltage to several low DC voltages. These voltages are used to operate a driver circuit, 13, which powers the light emitting diodes. The brightness of the light emitting diodes is controlled by the ratio of the on time to the off time from the driver circuit, which is controlled by the setting of the brightness potentiometer, 14. Another driver circuit, 15, also controls the brightness of the reticle illumination light emitting diodes in a similar manner using another brightness potentiometer, 16.

ALTERNATIVE EMBODIMENTS

Figure 5:
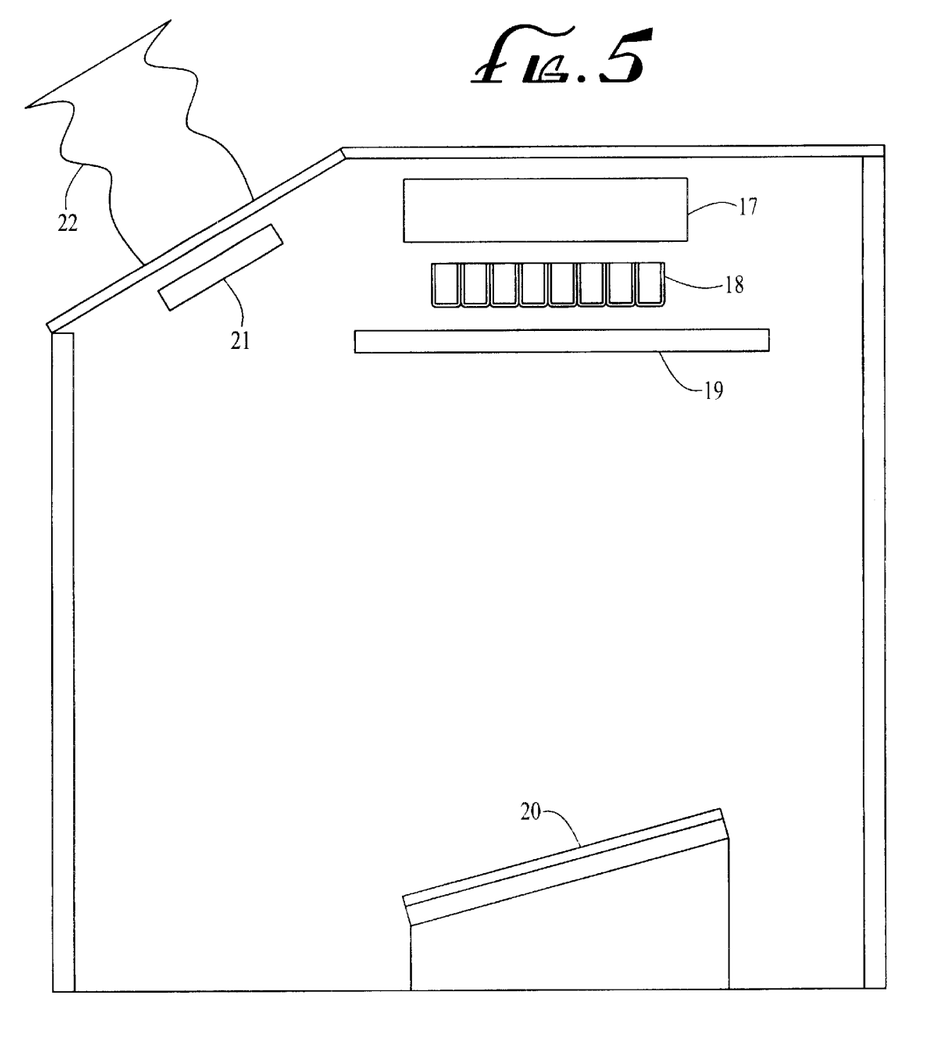
FIG. 5 shows the optical path with the placement of the excitation light source over the top of the chamber so the fluorescence of the samples can be viewed directly from the bottom.

Several other configurations are possible. Referring to FIG. 5, the excitation light source, 17, is placed over the top of the chambers, 18. The fluorescence from the samples is viewed directly from the bottom of the chambers through the reticle assembly, 19, via the mirror assembly, 20, the analyzer filter assembly, 21, and the eyepiece assembly, 22. The power source for the excitation light source is the same as in the preferred embodiment.

Figure 6:
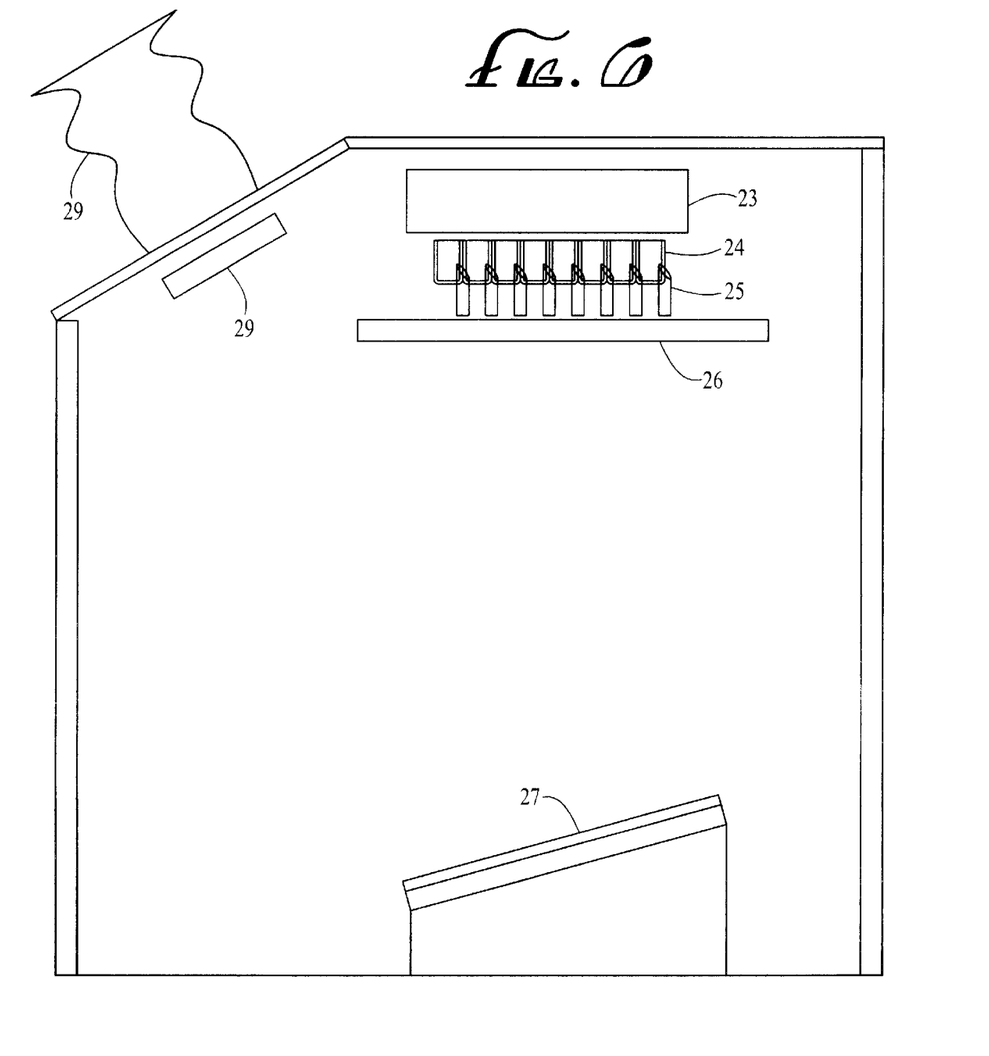
FIG. 6 shows an alternate optical path with the fiber optic light guide placed next to the sample chamber and the fluorescence is viewed from the bottom.
Figure 7:
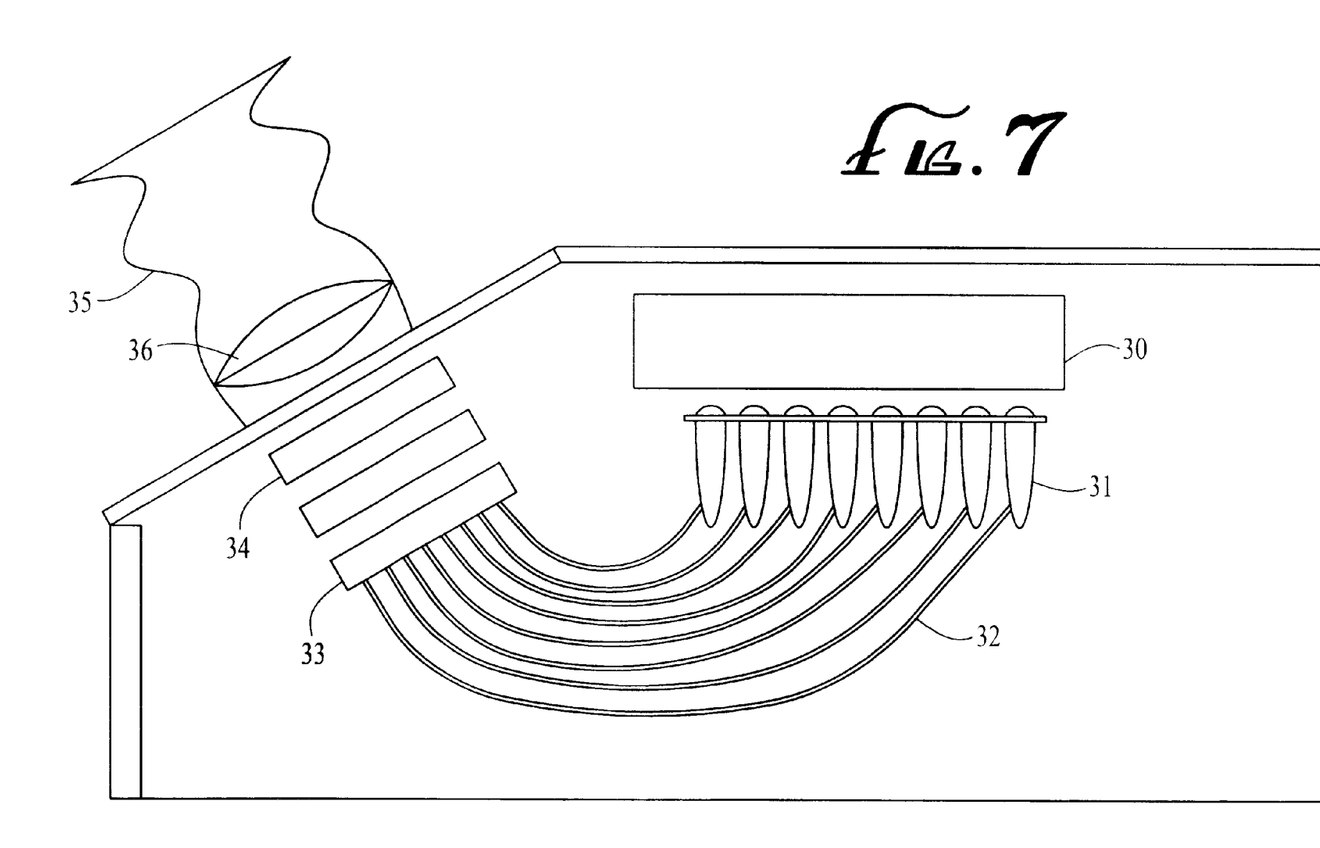
FIG. 7 shows a configuration with the excitation light source over the top chamber which are closed at the bottom. The fluorescence from the samples are viewed via flexible fiber optics light guides through a reticle assembly, an analyzer assembly and the eyepiece which contains an adjustable magnifier assembly.

The configuration in FIG. 6 is similar to the above two configurations in that the sample chambers are excited from the top by the excitation light source, 23. The chambers, 24, are closed to light at the bottoms and the fluorescence is coupled from the sides of the chambers via a fiber optic light guide assembly, 25, similar to the ones in the preferred embodiment. The fluorescence from the samples coupled through the fiber optic light guide assembly is viewed through the reticle assembly, 26, via the mirror assembly, 27, the analyzer filter assembly, 28, and the eyepiece assembly, 29. FIG. 7 shows a configuration in which the excitation light source, 30, is over the top of the chambers, 31, which are again closed at the bottom. The fluorescence from the samples coupled through a flexible fiber optic light guide assembly, 32. the ends of the fibers are viewed through a the reticle assembly, 33, the analyzer filter assembly, 34, and the eyepiece assembly, 35, which contains an adjustable magnifier assembly, 36.

Figure 8:
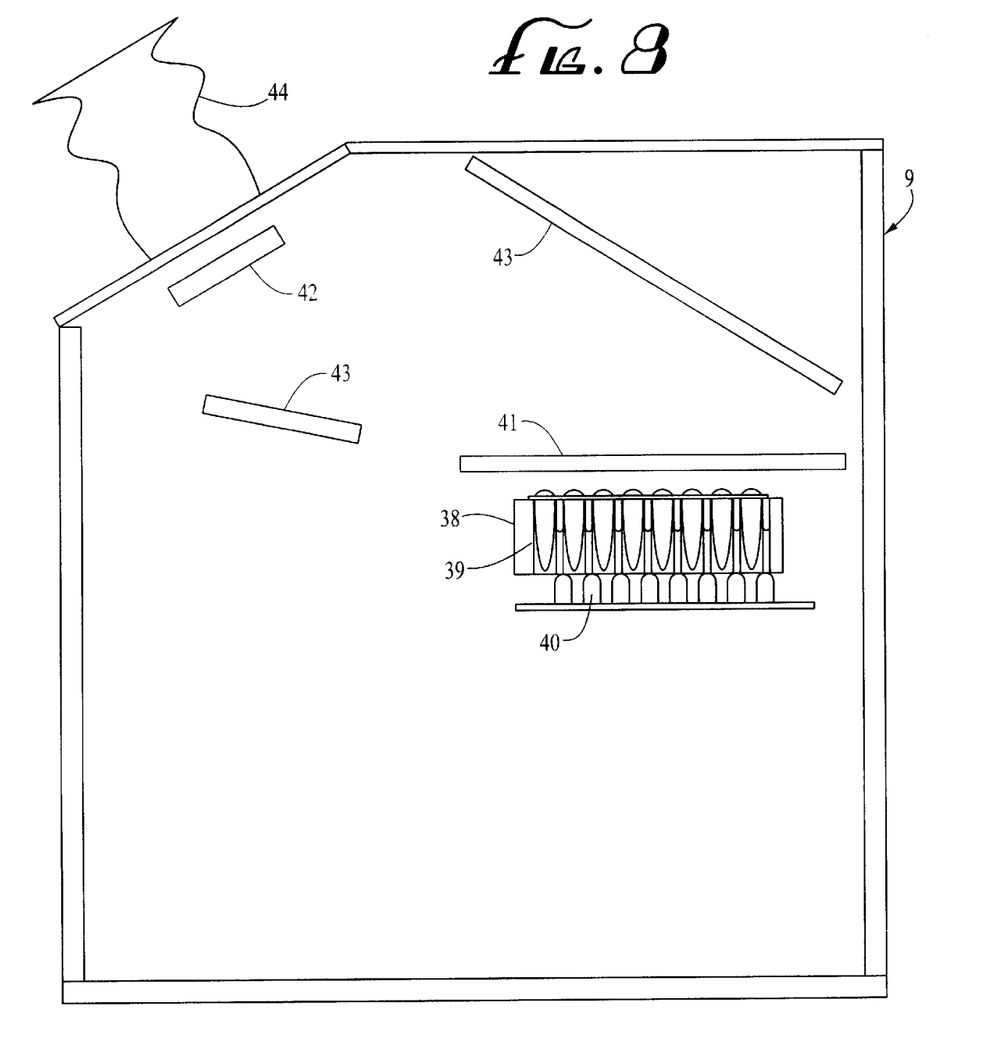
FIG. 8 shows the sample vials fit into the excitation light source chamber consisting of a colored plastic block with reflective prisms molded into it. These prisms reflect the light from the LEDs sideways into the samples. the fluorescence is viewed through the reticle assembly, the analyzer filter assembly, a mirror assembly and the reflected image is viewed into the eyepiece assembly.

Another embodiment configuration is as shown in FIG. 8. the sample vials, 37, fit into the excitation light source chambers, which consists of a colored filter plastic block, 38, with reflective prisms, 39, molded into it. These prisms reflect the light from the LEDs, 40, sideways into the samples. The fluorescence is viewed through the reticle assembly, 41, and the analyzer filter assembly, 42. A mirror assembly, 43, reflects the image into the eyepiece assembly, 44.

Figure 9:
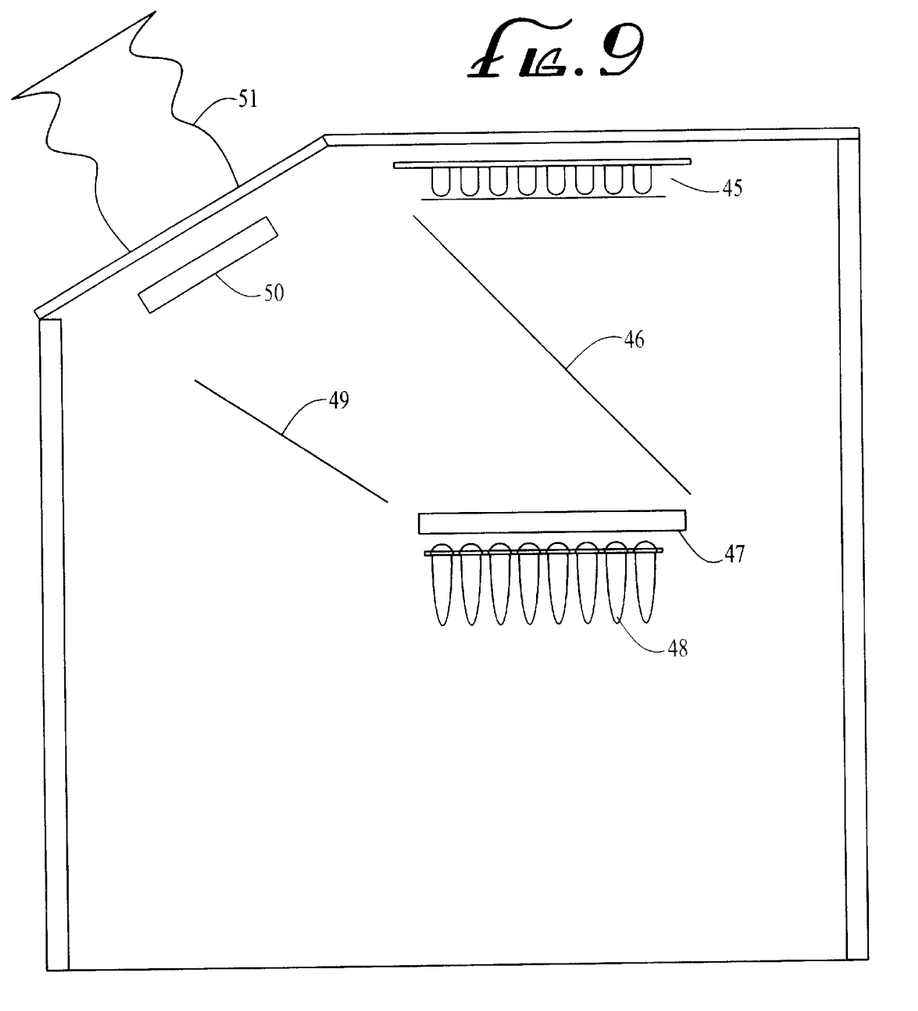
FIG. 9 shows the excitation light source illuminates the samples through a beam splitter assembly, retical assembly and the fluorescence from the samples is reflected back off the beam splitter assembly into the mirror assembly that reflects the light through the analyzer filter assembly and into the eyepiece assembly.

Yet another configuration is as follows. The excitation light source, 45, illuminates the samples, 48, through a beam splitter assembly, 46, and the reticle assembly, 47. The fluorescence from the samples is reflected back off of the beam splitter assembly into a mirror assembly 49 that reflects the light through the analyzer filter assembly 50 and into the eyepiece assembly 51.

Figure 10:
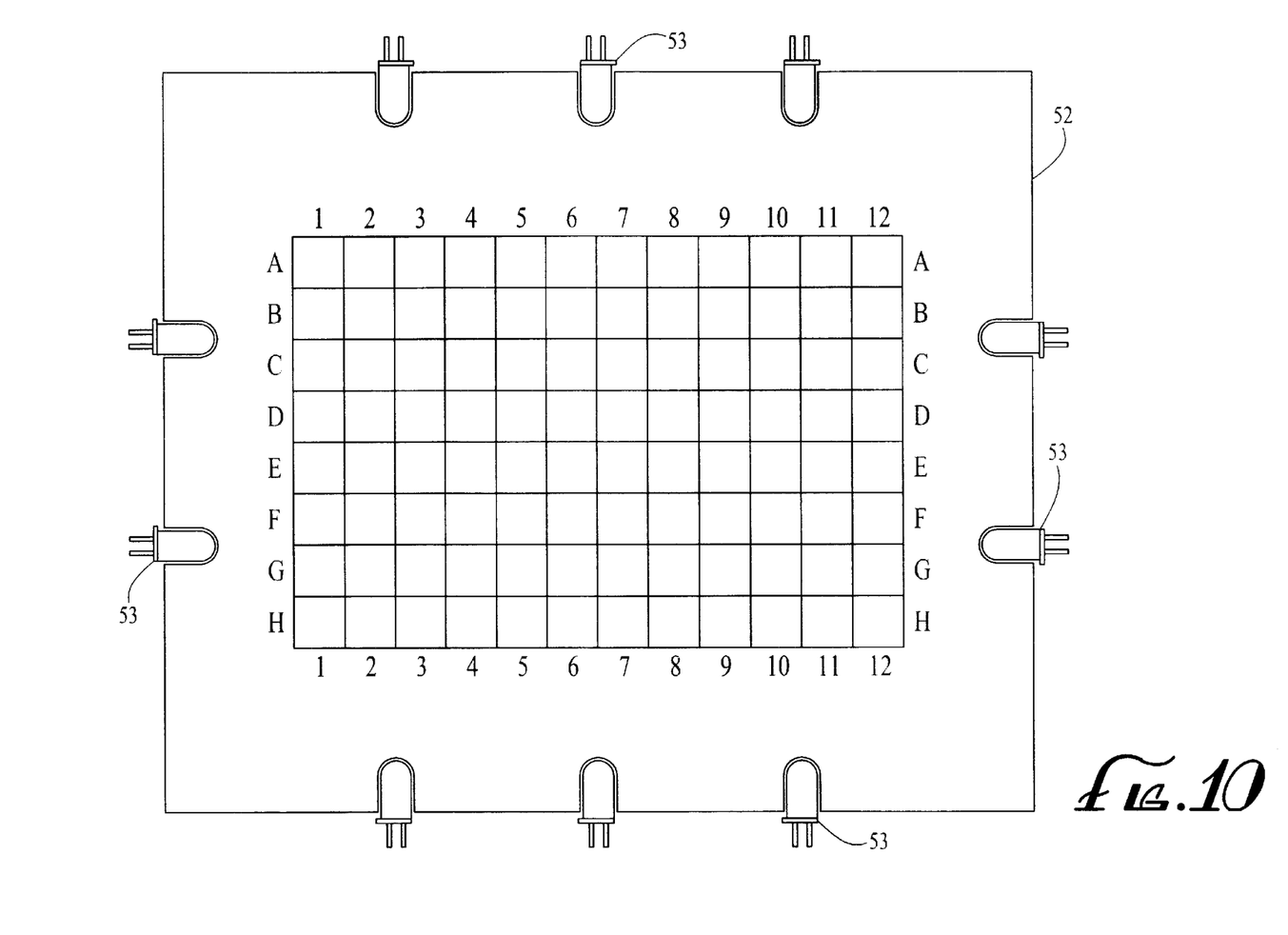
FIG. 10 shows the reticle assembly with illumination provided by a series of light emitting diodes.

FIG. 10 shows the reticle assembly consisting of the reticle 52 which is a transparent plate which has the grid pattern etched onto one surface. Illumination is provided by a series of light emitting diodes 53 around the edge of the plate.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. An instrument for detecting, visualizing and documenting fluorescence of molecular beacons reactions in a PCR strip or a PCR plate, said instrument comprising:
   at least one clear chamber holding a sample to be detected;
   a power supply to provide required voltages for the system;
   an adjustable light source for excitation of said sample to produce a characteristic wavelength;
   optical filters to accept and control said characteristic wavelength;
   a view port to view a reaction produced by said characteristic wavelength;
   a camera in said view port to photograph said reaction;
   a reticle adjacent to said chamber to identify the position of said sample;
   a variable light source for illumination of said reticle; and
   an optics and mirror assembly in association with said optical filters to provide viewing of said sample.

2. An instrument according to claim 1, wherein said adjustable light source includes an excitation light source assembly consisting of a set of light emitting diodes, an optical fiber light guide, an optical filter assembly residing below said chamber whereby a fiber optics light guide directs said excitation light into said chamber from sides thereof and whereby said entire assembly is replaceable for different types of molecular beacons.

3. An instrument according to claim 1, wherein said adjustable light source includes an excitation light source assembly that consists of a set of light emitting diodes placed over said chambers and fluorescence from said detected sample is viewed directly from beneath said chamber through said reticle via said mirror assembly.

4. An instrument according to claim 1, wherein said adjustable light source consists of a set of light emitting diodes that illuminates said sample through a beam splitter assembly and said reticle assembly whereby fluorescence from said sample is reflected back from said beam splitter assembly into said optic and mirror assembly which reflects light through said analyzer filter assembly and into said camera.

5. An instrument according to claim 1, with an adaption plate for directly viewing the molecular beacons samples.

6. An instrument according to claim 1, with an adaption plate for mounting a fixed or video camera with c mount lenses for recording fluorescence of said molecular beacons sample.

7. An instrument according to claim 1, with a laser etched grid and variable illumination control to identify said sample at a particular location.

8. An instrument according to claim 1, with an interchangeable assembly of light emitting diodes, fiber optics light guide and excitation filter assembly for use with different types of molecular beacons.

9. An instrument according to claim 1, with capability for viewing a single sample or a multiplicity of samples at the same time.

10. An instrument according to claim 1, with capability for photographing a single sample or a multiplicity of samples at the same time.

11. An instrument according to claim 1, with an optical train to visualize and photograph molecular beacons samples.

12. An instrument according to claim 1, where said excitation light source illuminates said sample through a beam splitter assembly and a reticle assembly whereby fluorescence from said sample is reflected from said splitter assembly into said optic and mirror assembly that reflects light through said analyzer filter assembly and into an optical viewer.

13. An instrument according to claim 1, including a reticle assembly consisting of a reticle network which is a transparent plate with a lined grid pattern etched onto a surface thereof whereby illumination is provided by a series of light emitting diodes around an edge of said plate.

* * * * *